United States Patent
Chalkiadakis et al.

(10) Patent No.: US 9,579,318 B2
(45) Date of Patent: Feb. 28, 2017

(54) HISTAMINE 4 RECEPTOR PARTIAL AGONISTS, INVERSE AGONISTS OR ANTAGONISTS FOR USE IN TREATING NON-AUTOIMMUNE UVEITIS

(71) Applicant: UCL BUSINESS PLC, London (GB)

(72) Inventors: Spyridon Chalkiadakis, London (GB); Virginia Calder, London (GB)

(73) Assignee: UCL BUSINESS PLC, London (GB)

( * ) Notice: Subject to any disclaimer, the term of this patent is extended or adjusted under 35 U.S.C. 154(b) by 0 days.

(21) Appl. No.: 14/424,927

(22) PCT Filed: Sep. 2, 2013

(86) PCT No.: PCT/GB2013/052300
§ 371 (c)(1),
(2) Date: Feb. 27, 2015

(87) PCT Pub. No.: WO2014/033480
PCT Pub. Date: Mar. 6, 2014

(65) Prior Publication Data
US 2015/0209348 A1    Jul. 30, 2015

(51) Int. Cl.
| | | |
|---|---|---|
| C07D 471/04 | (2006.01) |
| C07D 471/22 | (2006.01) |
| C07D 487/04 | (2006.01) |
| A01N 43/54 | (2006.01) |
| A61K 31/505 | (2006.01) |
| A01N 43/52 | (2006.01) |
| A61K 31/415 | (2006.01) |
| A61K 31/496 | (2006.01) |
| A61K 31/00 | (2006.01) |
| A61K 31/454 | (2006.01) |
| A61K 31/506 | (2006.01) |
| A61K 31/517 | (2006.01) |
| G01N 33/50 | (2006.01) |

(52) U.S. Cl.
CPC ............ *A61K 31/496* (2013.01); *A61K 31/00* (2013.01); *A61K 31/454* (2013.01); *A61K 31/506* (2013.01); *A61K 31/517* (2013.01); *G01N 33/502* (2013.01); *G01N 2333/705* (2013.01); *G01N 2500/04* (2013.01); *G01N 2500/10* (2013.01)

(58) Field of Classification Search
None
See application file for complete search history.

(56) References Cited

PUBLICATIONS

Lim, et. al., Molecular Pharmacology (2010), 77(5), 734-743.*
http://www.mayoclinic.org/diseases-conditions/uveitis/basics/definition/con-20026602 (last accessed Nov. 3, 2015).*

* cited by examiner

*Primary Examiner* — Jeffrey H Murray
(74) *Attorney, Agent, or Firm* — Stites & Harbison, PLLC; Mandy Wilson Decker; Sean P. Ritchie

(57) ABSTRACT

The invention provides a compound which is a histamine 4 receptor antagonist, partial agonist or inverse agonist, for use in the treatment of non-autoimmune uveitis. The compound preferably has a structural core comprising a substituted pyrimidine group, such as an aminopyrimidine, diaminopyrimidine or triaminopyrimidine group, a thienopyrimidine, a furopyrimidine, a benzimidazole, an aryl or heteroaryl-fused pyrimidine, an indole, a bicyclic heteroaryl-substituted imidazole or a quinazoline group.

13 Claims, 2 Drawing Sheets

Figure 1:
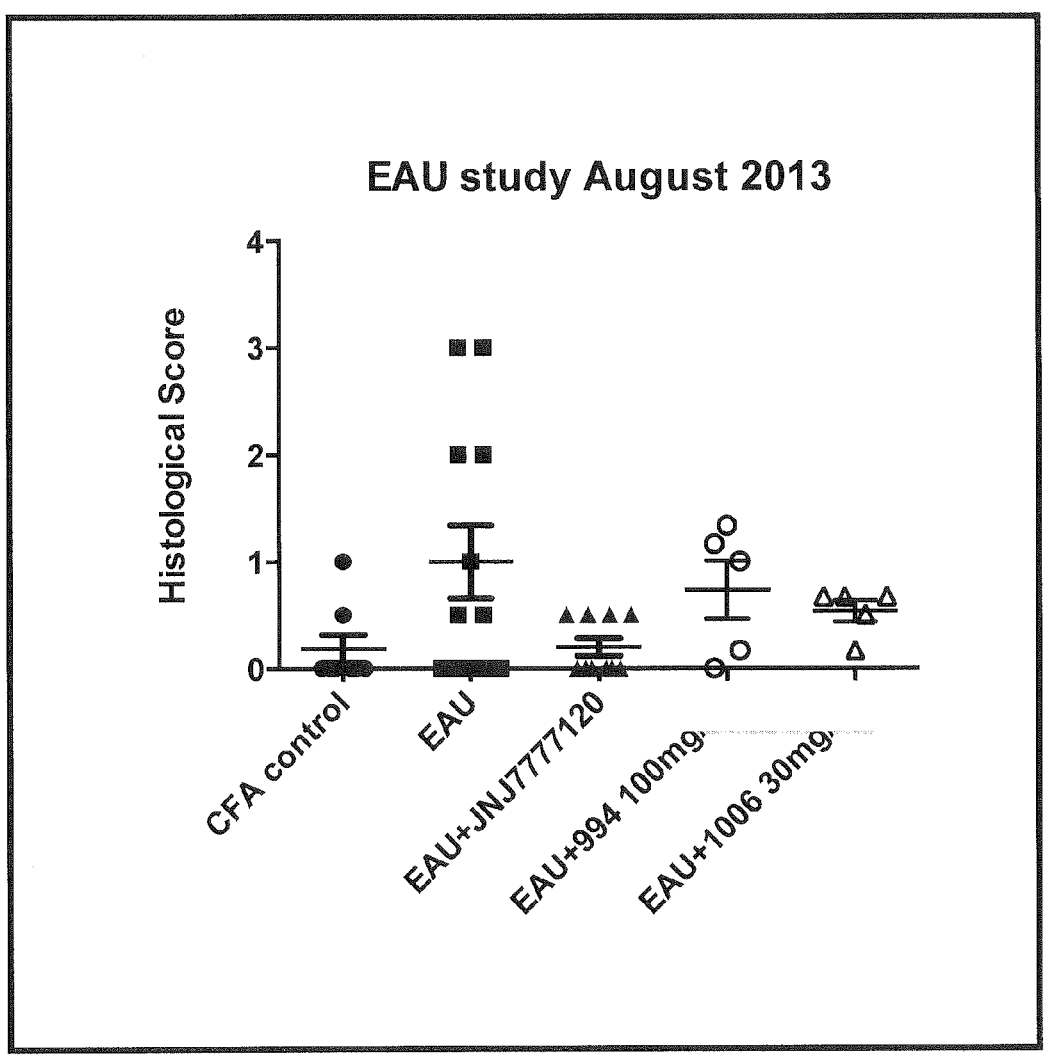

HISTAMINE 4 RECEPTOR PARTIAL AGONISTS, INVERSE AGONISTS OR ANTAGONISTS FOR USE IN TREATING NON-AUTOIMMUNE UVEITIS

FIELD OF THE INVENTION

The invention relates to a new medical use. In particular, it relates to the use of compounds which are antagonists, partial agonists or inverse agonists of the histamine 4 receptor (H4R) in the treatment of inflammatory diseases in which the inflammation involves neutrophils, in particular uveitis.

BACKGROUND TO THE INVENTION

Histamine is a pleiotropic mediator, involved in a variety of physiological processes including neurotransmission, endocrine and vascular functions. It is also intricately involved in inflammation, upon binding to one or more of the four histamine receptors (H1-4R). H4Rs are predominantly expressed by haemopoietic cells such as T cells, as well as mast cells, basophils, monocytes and neutrophils.

Considerable advances in understanding the role of H4R have been made since the development of H4R agonists and antagonists and studies with H4R knockout mice (Tiligada, Zampeli et al. 2009; Zampeli and Tiligada 2009). Evidence suggests that the H4R can be proinflammatory for several in vivo models of inflammation. In contrast, using a mouse model of airway hyper responsiveness, administration of the H4R agonist 4-methyl histamine was anti-inflammatory and reduced airway hyper responsiveness (Morgan, McAllister et al. 2007). In that in vivo model an increase in regulatory T cells (Treg) was also observed, suggesting a mechanism whereby H4R stimulation mediates anti-inflammatory responses. Single-nucleotide polymorphisms (SNPs, pronounced snip) analysis of patients with Systemic Lupus Erythematosus (SLE) and psoriasis has identified an association with human H4R (Yu, Shao et al. 2010), suggesting a link between H4R and clinical disease. In a recent study of H4R knockout mice induced for experimental autoimmune encephalomyelitis (EAE), a CD4+T cell-mediated mouse model of multiple sclerosis, it has been found that the H4R gene deficient mice demonstrated an increase in EAE disease severity and enhanced blood-brain barrier permeability, despite having similar numbers of effector CD4+ T cells (del Rio, Noubade et al. 2012). Interestingly, there were fewer Treg in the CNS of these mice, resulting in increased levels of effector Th17 cells. These data would agree with the hypothesis that H4R is playing an important role in regulating inflammation.

The inventors tested the efficacy of H4R antagonists in two models of uveitis: experimental autoimmiune uveitis (EAU) and endotoxin induced uveitis (EIU) and were surprised to find that they were effective against both conditions. EIU is an innate cell mediated condition, specifically it is mediated by neutrophils. It is brought about by injecting a model animal with bacterial endotoxin, a lipopolysaccharide (LPS). Experimental autoimmune uveitis is generally accepted to be T-cell mediated, and so it is surprising that the same antagonists were efficacious against both models.

A large number of H4R modulating compounds are known, and have in some instances been suggested (albeit not actually shown) to be of potential usefulness in autoimmune uveitis. Such modulators can be found, for example, in Sander et at (Bioorg. Med. Chem. (2009) 17, 7186), Schreeb et al. (Pharmazie (2013) 68, 521), Savall (Annual Meeting of the European Histamine Research Society, May 2013, Programme and Abstracts, p 48), Zampeli et at (Inflamm Res. (2009) 58, 285), US 2009/0075970, US 2005/0070550, US 2010/0240671, US 2007/0238771, EP 2270002 A1, WO 2007/031529, WO2009/056551, WO 2009/068512, WO 2009/077608, WO 2009/080721, WO 2009/115496. Lazewska et at (Frontiers in Bioscience (2012), S4, 967), WO2012/041860, WO2011/076878A1, WO2010/075270A1, WO2009/047255, WO2009/134726, WO2001/085786, WO2009/038673, WO2008/060766, WO2005/031308, WO2008/003702, WO2007/117401, WO2010/072829, WO2008/006974, WO2004/021999, WO2008/008359, WO2004/022537, WO2003/057919, WO2010/108059, WO2002/072548, WO2009/079001, WO2008/100565, WO2007/117400, WO2009/068512, WO2006/050965, WO2001/092485, WO2010/146173, WO2009/071625, WO2004/022060, and WO2004/066960. The contents of each of these documents, and in particular the H4R modulators disclosed therein, are incorporated herein in their entirety by reference.

SUMMARY OF THE INVENTION

The present invention provides a compound which is a histamine 4 receptor antagonist, partial agonist or inverse agonist, for use in the treatment of non-autoimmune uveitis. Non-autoimmune uveitis (which includes idiopathic uveitis and primary uveitis) is uveitis for which an autoimmune cause cannot be attributed. The term, as used herein, is intended to cover those forms of uveitis in which no substantial autoimmune aetiology can be determined, as well as those forms in which an autoimmune manifestation might be apparent, possibly in combination with other causative factors (including uveitis as a co-morbidity with inflammatory conditions, autoimmune or otherwise, affecting other tissues). The non-autoimmune uveitis is preferably also non-infectious uveitis. In preferred embodiments, the non-autoimmune uveitis is of the type in which no substantial autoimmune aetiology can be determined. Indeed, contrary to what is suggested in the prior art referred to above, there is not a strong autoimmune component in uveitis—only in posterior uveitis are T cells thought to be involved at the early stages of disease. However, detection of autoreactive T cells and/or antibodies are rarely found and are not used for clinical diagnosis or predictors of disease. As such, autoimmune uveitis would not seem to be relevant in the clinical setting. Autoimmune diseases are clinical entities with a well-defined immunological explanation. The prior art does not describe any clinical autoimmune uveitis with a well-defined immunological mechanism.

In embodiments, the compound has a structural core comprising a substituted pyrimidine group (such as an aminopyrimidine (e.g. 2-, 4-, or 6-aminopyrimidine), diaminopyrimidine or triaminopyrimidine, such as the amino-substituted pyrimidines disclosed in any of Sander et al (Bioorg. Med. Chem. (2009) 17, 7186), Schreeb et al. (Pharmazie (2013) 68, 521), Savall (Annual Meeting of the European Histamine Research Society, May 2013, Programme and Abstracts, p 48), Zampeli et al (Inflamm Res. (2009) 58, 285), US 2009/0075970, US 2005/0070550, US 2010/0240671, US 2007/0238771, EP 2270002 A1, WO 2007/031529, WO2009/056551, WO 2009/068512, WO 2009/077608, WO 2009/080721, WO 2009/115496, Lazewska et al (Frontiers in Bioscience (2012), S4, 967; for example the compounds disclosed therein as being from Palau Pharma), WO2012/041860, WO2011/076878A1, WO2010/075270A1, WO2009/047255, WO2009/134726, WO2001/085786, WO2009/038673, WO2008/060766, WO2005/031308, WO2008/003702, WO2007/117401, WO2010/072829, WO2008/006974, WO2004/021999, WO2008/008359, WO2004/022537, WO2003/057919, WO2010/108059, WO2002/072548, WO2009/079001, WO2008/100565, WO2007/117400, WO2009/068512, WO2006/050965, WO2001/092485, WO2010/146173, WO2009/071625, WO2004/022060, and WO2004/066960). In particular embodiments, the compound may have a structural core comprising a 2,4,6-triaminopyrimidine (such as the compounds of Schreeb et al (see above), in particular those shown in Table 1 therein, or such as the compounds of Sander et al (see above), in particular compounds 15, 16, 19-38 therein), a 2,4-diaminopyrimidine (such as the compounds of Sander et al (see above), in particular compound 14 therein), a 2-aminopyrimidine (such as the 6-alkyl-2,4-diaminopyrimidines described by Savall (see above), and in particular JNJ 39758979, or such as the substituted aminopyrimidines shown in US 2010/0240671, Formula I), a 4-aminopyrimidine (such as those disclosed in WO 2007/031529, WO2009/056551, WO 2009/068512, WO 2009/077608, WO 2009/080721, WO 2009/115496 or Lazewska et al (above)), a thienopyrimidine (such as those shown in US 2009/0075970, Formula I), a furopyrimidine (such as those shown in US 2009/0075970, Formula I), a benzimidazole (such as those shown in US 2005/0070550, Formula I and Formula II, or such as those shown in US 2007/0238771, Formula I), an aryl or heteroaryl-fused pyrimidine (such as those shown in US 2010/0240671, Formula XI), an indole (such as those shown in US 2007/0238771, Formula I), a bicyclic heteroaryl-substituted imidazole (such as those shown in US 2009/0156613, Formula I) or a quinazoline group (such as those shown in EP 2270002A1, Formula I). Also of use according to the invention are any of the H4R modulators disclosed in Lazewska et al (above), whether or not they fall within the above structural definitions. The structures and other relevant aspects of the compounds identified above as being disclosed in these documents are incorporated herein by reference.

In certain embodiments, the compound for use may be selected from thioperamide; JNJ 7777120 (1-[(5-chloro-1H-indol-2-yl)carbonyl]-4-methylpiperazine); VUF-6002 (1-[(5-chloro-1H-benzimidazol-2-yl)carbonyl]-4-methylpiperazine); A987306 having the structure

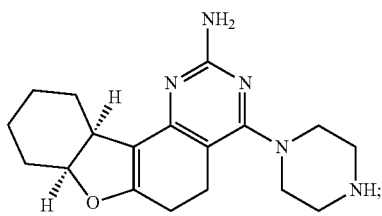 [SMILES: Nc1nc2c(c(N3CCNCC3)n1)CCC1=C2[C@@H]2CCCC[C@@H]2O1]

A943931 having the structure

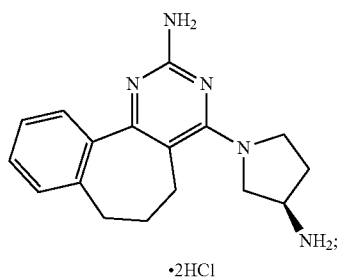 [SMILES: Nc1nc2c(c(N3CC[C@@H](N)C3)n1)CCCc1ccccc1-2]

JNJ10191584 having the structure

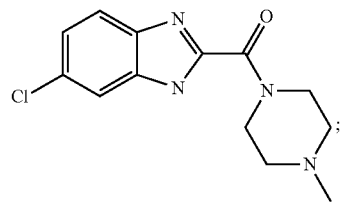 [SMILES: CN1CCN(C(=O)c2nc3ccc(Cl)cc3[nH]2)CC1]

INCB38579 (1-(7-(2-amino-6-(4-methylpiperazin-1-yl)pyrimidin-4-yl)-3,4-dihdroisoquinolin-2(1H)-yl)-2-cyclopentylethanone); JNJ28307474 (5-fluoro-4-methyl-2-{5-methyl-2-[4-(1-methyl-piperidin-4-yl)-butoxy]-pyridin-4yl}-1H-benzoimidazole);

994 having the structure

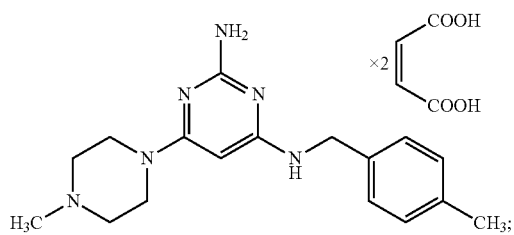

1006 having the structure

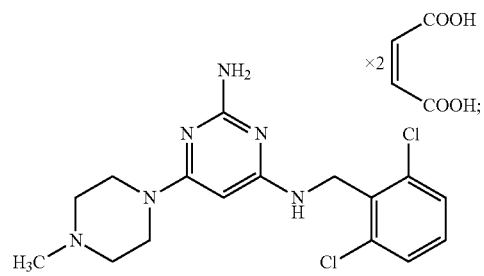

and 1012 having the structure

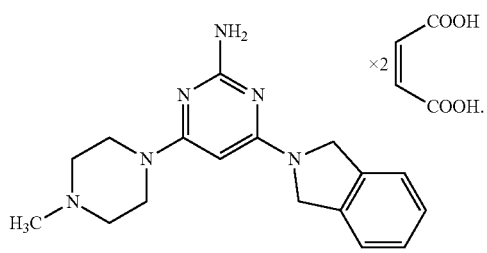 [SMILES: CN1CCN(c2cc(N3Cc4ccccc4C3)nc(N)n2)CC1 ; O=C(O)/C=C\C(=O)O]

In a particular embodiment, the compound is JNJ7777120 or a functional derivative or analogue thereof. In another particular embodiment, the compound is 994, 1006 or 1012, and in particular 994.

In an embodiment, the uveitis is intermediate uveitis, panuveitis, posterior uveitis, anterior uveitis (including chronic anterior uveitis, subacute anterior uveitis, or acute anterior uveitis). In another embodiment, the uveitis is anterior uveitis or posterior uveitis (in each instance, subacute, acute or chronic forms), particularly anterior uveitis (of all sub-types).

In particular embodiments, the uveitis is intermediate uveitis, panuveitis or posterior uveitis. In alternative embodiments, the uveitis is anterior uveitis (including chronic anterior uveitis, subacute anterior uveitis, or acute anterior uveitis).

In another aspect, the invention provides a method of treating non-autoimmune uveitis, the method comprising administering an effective amount of a compound which is a histamine 4 receptor antagonist, partial agonist or inverse agonist to a subject having uveitis.

The various embodiments of the use defined above are also applicable, alone or in any compatible combination, to the method of this aspect of the invention.

The method of the invention may comprise administering or delivering the compound to an eye of a subject having uveitis, in the form of eye drops, by injection into the eye, or by oral administration.

The invention also provides a method of identifying a candidate compound suitable for use in treatment of non-automimmune uveitis, the method comprising providing at least one test compound, determining whether the test compound is a histamine 4 receptor antagonist, partial agonist or inverse agonist, and selecting such a test compound as a candidate compound accordingly. In an embodiment, the binding and/or efficacy of the test compound at a histamine 4 receptor or analogue thereof is determined.

The invention provides a histamine 4 receptor antagonist, partial agonist or inverse agonist for use in the treatment of uveitis.

Also provided is a method of treating uveitis comprising administering an effective amount of a histamine 4 receptor antagonist, partial agonist or inverse agonist to a subject in need thereof.

Histamine H4 receptor (H4R) antagonists are well known in the art. H4R is, like the other three histamine receptors (H1, H2 and H3), a member of the G protein-coupled receptor superfamily. Primarily expressed on immune cells (bone marrow and white blood cells), it affects Th2 responses, dendritic cell functions, eosinophil and mast cell chemotaxis, and regulates neutrophil release from bone marrow and subsequent infiltration in the zymosan-induced pleurisy model. It seems to do this by the mechanism of $G_i$-coupled decrease in cAMP ($G_i$ alpha subunit [or $G_i/G_0$ or $G_i$ protein] is a heterotrimeric G protein subunit that inhibits the production of cAMP from ATP). It is also expressed in the colon, liver, lung, small intestine, spleen, testes, thymus, tonsils, and a trachea.

A receptor antagonist is a type of receptor ligand or drug that does not provoke a biological response itself upon binding to a receptor, but blocks or dampens agonist-mediated responses. In pharmacology, antagonists have affinity but no efficacy for their cognate receptors, and binding will disrupt the interaction and inhibit the function of an agonist or inverse agonist at receptors. The term H4R antagonist encompasses compounds which bind to the H4R and act directly upon it, and compounds which reduce the effect of H4R agonists by indirect action, for example those which bind to agonists of the H4R and reduce their impact.

A partial agonist is an agonist of a receptor which bind but only have partial efficacy at the receptor relative to the full agonist. As a result, they can compete with full agonists for binding and thereby act as a competitive antagonist.

An inverse agonist is an agent that binds to a receptor but has the opposite pharmacological effect as an agonist.

Examples of H4R antagonists, partial and inverse agonists include: Thioperamide

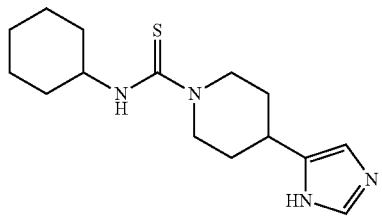 [SMILES: S=C(NC1CCCCC1)N1CCC(c2cnc[nH]2)CC1]

JNJ 7777120 (1-[(5-Chloro-1H-indol-2-yl)carbonyl]-4-methylpiperazine)

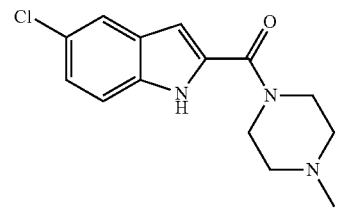 [SMILES: CN1CCN(C(=O)c2cc3cc(Cl)ccc3[nH]2)CC1]

VUF-6002 (1-[(5-chloro-1H-benzimidazol-2-yl)carbonyl]-4-methylpiperazine)

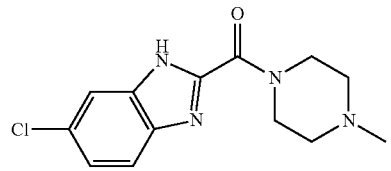 [SMILES: CN1CCN(C(=O)c2nc3ccc(Cl)cc3[nH]2)CC1]

A987306

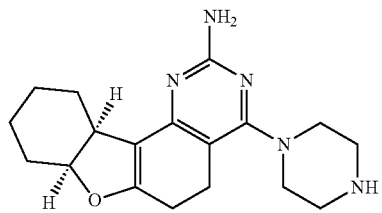 [SMILES: Nc1nc2c(c(N3CCNCC3)n1)CCC1=C2[C@@H]2CCCC[C@@H]2O1]

A943931

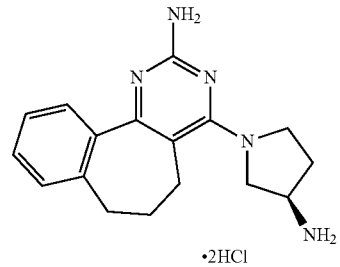 [SMILES: Nc1nc2c(c(N3CC[C@@H](N)C3)n1)CCCc1ccccc1-2]

JNJ10191584

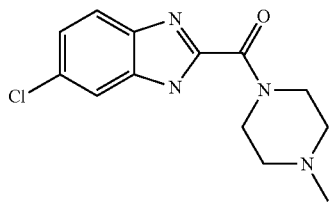 [SMILES: CN1CCN(C(=O)c2nc3ccc(Cl)cc3[nH]2)CC1]

INCB38579
(1-(7-(2-amino-6-(4-methylpiperazin-1-yl) pyrimidin-4-yl)-3,4-dihdroisoquinolin-2(1H)-yl)-2-cyclopentyletha-none)

JNJ28307474, as described in Cowden, J., et al., Journal of Investigative Dermatology (2010) 130, 1023-1033

The compounds 994, 1006 and 1012, as described in Sanders K., et al., Bioorganic & Medicinal Chemistry 17 (2009) 7186-7196.

Preferably the H4R antagonist, partial agonist or inverse agonist is one of JNJ7777120, JNJ28307474, 994, 1006 and 1012, or a functional derivative, that is to say a derivative having similar antagonist or agonist activity, thereof. It is most preferably JNJ7777120 or a functional derivative thereof.

Other compounds may be tested for their antagonist, partial agonist or inverse agonist properties at the H4R using standard techniques for identifying binding and efficacy. Such techniques are known in the art.

Uveitis means inflammation of part or parts of the uvea, including the iris, ciliary body and choroid, but may also involve inflammation of adjacent structures, including for example the retina, sclera and optic nerve. In particular, the uveitis treated may be anterior uveitis, affecting the iris in particular, posterior uveitis, affecting the choroid in particular and occasionally the retina, or may be pars planitis, which is inflammation of the pars plana between the coloured part of the eye (iris) and the choroid. Uveitis may be caused by a number of conditions or factors, such as infection or exposure to toxins, and may be associated with certain autoimmune disorders including rheumatoid arthritis or ankylosing spondylitis. As mentioned above, the use of the H4R modulators according to the invention is preferably in uveitis which is non-infectious.

The method of treating uveitis may involve administering the H4R antagonist to the eye, for example in the form of eye drops, or may involve administering it by injection into the eye, sub-conjunctival administration, oral administration, or administration by any other route.

Uveitis Stratification

Noninfectious Uveitis describes a group of intraocular inflammatory diseases in which there is inflammation of the uveal tract, retina and/or choroid. Visual loss can occur due to the irreversible loss of photoreceptor cells, and the ophthalmologist aims to arrest the inflammation as early as possible to prevent further immune-mediated tissue damage.

Due to the anatomical positioning of the retinal layers, the disease can predominantly affect the posterior segment (Posterior uveitis) or the anterior segment (Anterior uveitis) or it can involve both anterior and posterior segments (Intermediate uveitis, Panuveitis) and clinical severity ranges from mild (Fuchs heterochromic iridocyclitis) to severe (eg Chronic Posterior Uveitis). Uveitis can be sub-acute, acute or chronic, and may be sub-clinical or clinically significant. Uveitis can occur as part of a systemic disease (Behçet's disease) or can occur in the absence (i.e. primary or idiopathic uveitis) of any systemic abnormalities (Pars Planitis, Idiopathic Anterior Uveitis).

Uveitis Treatment

Steroids were traditionally the mainstay of anti-inflammatory therapy for uveitis, given as a high dose orally and then tapering the dose as quickly as possible. Steroids can have very serious side-effects for the eye when used long term, increasing intraocular pressure, causing glaucoma and cataract formation. Cyclosporin A and other steroid-sparing therapies are also given to reduce or replace the level of steroids required to dampen the inflammatory process. The recent development of more specific anti-inflammatories (eg anti-TNFα) have provided a greater choice for the ophthalmologist, although they are expensive and are not effective for all patients, and are often given to those patients with severe disease who are not responding to the more conventional therapies. Hence steroids are still the first choice for treatment and there is an urgent need for safer, more effective anti-inflammatory therapies for uveitis. In addition, the clinical assessment of patients with milder forms of uveitis may go on to develop more severe or chronic forms of disease due to lack of accurate, sensitive diagnostic methods like fundus fluorescein angiography (FFA), indocyanin green angiography (ICG) or optical coherence tomography (OCT) scans.

Experimental Models

Experimental autoimmune uveoretinitis (EAU) describes a model of retinal immune-mediated disease following immunization of retinal proteins emulsified in adjuvant. EAU can be induced in a number of animal species and the inflammation that follows shares many anatomical features with that seen in uveitis affecting the posterior segment in man. EAU in mice is considered to be a good model for investigating the cellular mechanisms involved and the role of the blood-retinal barrier in posterior uveitis, with early signs of disease detectable by 10-12 days post immunization, peak inflammation of the retina at 14-21 days, and then an attenuation occurring. In mice, some strains are more susceptible to developing disease than others, with B10RIII mice developing a severe acute form of disease whereas C57B1/6 mice display a milder, but more chronic form where disease can be detected histologically up to 55 days post immunization. It should be noted that the different strains of mice exhibit different time courses and disease severities which can also differ from lab to lab, depending on the immune status of the mice, the immunizing peptide used etc.

In the EAU model, the inflammation takes 12-14 days to become apparent since it involves the slow, but highly specific, adaptive immune response (T cells). The cells driving the disease are a subset of T cells (CD4+), whilst at later stages of disease other proinflammatory cells including macrophages and neutrophils become involved. EAU can even be induced by immunizing with retinal antigen-specific CD4+T cells, the definitive evidence that EAU is a T cell-mediated disease model. However in the chronic C57B1/6 model we have used, there is an involvement of other leucocytes after the initial acute phase of disease ie after 14-17 days.

For investigating the effects of anti-inflammatory drugs, in the majority of studies the mice are pretreated with compounds prior to inducing disease, or are treated throughout disease development. In many instances, anti-inflammatory compounds are effective in treating EAU, downregulating retinal inflammation. However, EAU does not completely replicate the timecourse of immune-mediated disease seen in man (which lasts many years), most patients appear in clinic when disease has already developed and they may also have a systemic disease which complicates their anti-inflammatory treatment.

Nevertheless, the data reported herein have been derived from a C57Bl/6 mouse model of EAU that is chronic, clinically mild where the disease was established prior to treating, ie therapeutically as opposed to prophylactically. The results support H4R-targetting therapy for the attenuation of retinal inflammation similar to inflammation seen in patients with intermediate uveitis, panuveitis and posterior uveitis.

Experimental intermediate uveitis (EIU) is a very different model in which lipopolysaccharide (LPS; endotoxin) is given either systemically or intraocularly and within 24-48 hours, a very severe inflammation of the anterior segment occurs. This model is thought to display characteristics of subacute and acute anterior uveitis since the inflammatory cells are restricted to the anterior segment and only infiltrate the inner limiting membrane and nerve fibre layer but do not infiltrate the remaining outer retinal layers.

The EIU model is a rapid inflammatory response to endotoxin which peaks within 24-48 hours, and involves the rapid infiltration of innate leucocytes such as neutrophils as well as local activation of macrophages and tissue-resident mast cells. Hence this model is useful when studying anterior uveitis due to the similar types of proinflammatory cells involved in both.

In our EIU model, which is induced by systemic immunization with LPS, there is a marked infiltration of cells which can be detected at 24-48 hours post disease induction. In this model we pretreated the mice with the H4R compounds prior to inducing disease since the disease window is relatively short. The data reported herein reflect potential therapeutic application for patients with anterior uveitis.

Inflammatory Mechanisms in Uveitis

In uveitis affecting man, it is believed that posterior uveitis is a T cell-mediated disease, since many of the posterior uveitis patients (ie those with intermediate uveitis, panuveitis and posterior uveitis) respond to treatment with cyclosporine A, which specifically targets the activation of T cells. Additional support for a T cell-driven process is the finding of enhanced expression of HLA class II molecules expressed locally in the retina of uveitis patients, which are not detected in normal retinal tissues, and are molecules which is required for activation of T cells within tissues by local cells. The third and final line of evidence to support a role for T cells in this form of uveitis is the genetic linkage, where the disease is has an inheritable component, found at the HLA-DR gene locus. Due to these characteristics, this form of uveitis is usually thought to be similar to other immune-mediated diseases (rheumatoid arthritis, multiple sclerosis and Type 2 diabetes).

For those patients with anterior uveitis (ie subacute and acute anterior uveitis), the importance of T cells in driving disease is less clear whilst the genetic predisposition involves the HLA-B27 locus, which is important for more general inflammatory processes, including cells of the innate system (leukocytes such as neutrophils, macrophages etc). Cyclosporin A is not always used for these patients whilst anti-TNFα and other broad spectrum anti-inflammatories are used.

Inflammatory Mechanisms in Experimental Models

The fact that the results reported herein demonstrate a significant amelioration of disease in both models strongly suggests a targeting of the leucocyte arm, such as the neutrophils.

Figure 2:
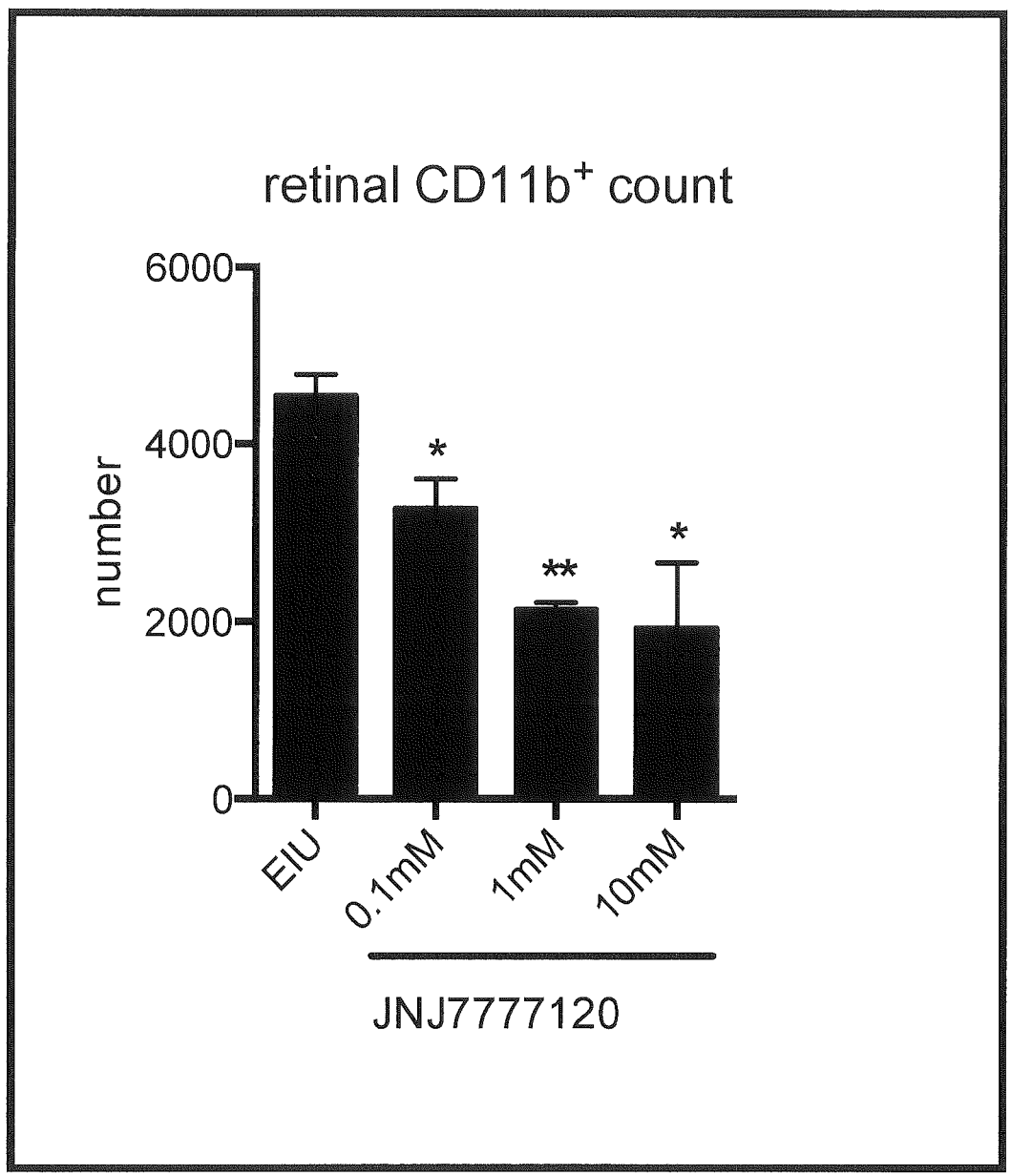

The present invention will now be described in more detail by way of example only, and with reference to the following drawings, of which:

FIG. 1 shows the results of tests conducted in the EAU model with H4R modulator JNJ7777120 (16 mg/kg) and modulators 994 (100 mg/kg (referred to as '100 mg' in the figure)) and 1006 (30 mg/kg (referred to as '30 mg' in the figure)). ctl=control; and FIG. 2 shows the results of tests conducted in the EIU model with the same H4R modulator as in FIG. 1 (JNJ7777120).

EXAMPLES

Methods

Two Experimental Models were Investigated for the Therapeutic (Ie Treat after Disease is Established) Effects of JNJ777120, an H4R Modulator (Antagonist), and Two Amino-Substituted Pyrimidine H4R Modulator Compounds (994 and 1006).

Example 1

Experimental Autoimmune Uveitis

Experimental autoimmune uveitis (EAU) is a CD4+T cell-mediated retinal inflammation induced in mice by immunising with a retinal antigen. Whilst CD4+T cells are crucial for disease induction, it is now established in the literature (see Dick et al 2012) that tissue resident cells (microglia, macrophages) and infiltrating inflammatory cells (CD11b+granulocytes) contribute to the perpetuation of the inflammation in the C57BL/6 mouse, where evidence of retinal inflammation can be observed up to day 56 post immunization.

In our study EAU was induced in C57Bl/6 mice using subcutaneous administration of IRBP peptide emulsified in complete Freund's adjuvant (CFA) supplemented with 1.5 ug/mL mycobacterium, and intraperitoneal immunisation with Pertussis toxin. Clinical signs of EAU disease were monitored using non-invasive retinal fundus imaging (TEFI) until signs of retinal inflammatory disease were observed (usually by day 14). At this point mice were divided into treatment groups. A total of 45 mice were used, with groups as follows: CFA controls n=4; EAU controls n=6; JNJ 7777120 16 mg/kg n=5; 994 10 mg/kg n=5; 994 30 mg/kg n=5; 994 100 mg/kg n=5; 1006 10 mg/kg n=5; 1006 30 mg/kg n=5; 1006 100 mg/kg n=5. Each treatment group of mice received 5 intraperitoneal doses of compound, once per day, until day 19 when eyes were harvested. At this point eyes were processed and fixed, and histological sections were prepared.

Data from the control groups and the H4R modulator-treated groups are shown in FIG. 1. Histological scoring by light microscopy was done according to established methods (Gegg et al, 2005) where a score of 1.0 reflects inflammatory cells present in the vitreous cavity but not throughout the retinal layers, and the photoreceptor layer is as normal. A score of 2.0 reflects cells within the outer retinal layers, with some granuloma formation. A score of 3.0 reflects cells within the photoreceptor layer, some retinal folding, a focal loss of photoreceptor cells. Results are shown in FIG. 1 below. The JNJ7777120 compound reduced the histological scores to control levels, as did the 994 and 1006 compounds. This is an impressive effect since disease was already established. In most treatment studies mice are pretreated with drug prior to inducing EAU.

Example 2

Endotoxin Induced Uveitis

EIU is a more acute form of anterior uveitis, induced by intraperitoneal immunization with LPS (endotoxin), and clinical signs of uveitis can be observed within 24-48 hours post immunisation. Due to the narrow time frame of disease, in our study mice (n=2 per group) were pretreated with three different concentrations of JNJ777120 compound (0.1, 1.0 and 10.0 mM) given twice daily as eyedrops for 3 days prior to inducing EIU, and eyes harvested 24 hours later. In this study, retinas were dissected from each eye and single cell suspensions prepared for staining with CD11b (to stain for granulocytes), and analysed by flow cytometry, Each eye was kept separate, so results are shown as means of 4 retinae in each group, in comparison with 6 eyes from 3 EIU non-treated control mice. Numbers of CD11b+ cells (a pan granulocyte marker) are shown in FIG. 2. The JNJ compound significantly decreased the levels of infiltrating granulocytes (mainly neutrophils) and this was impressive as the compound was administered topically as eyedrops.

REFERENCES 1. del Rio, R., R. Noubade, et al. (2012). "Histamine H4 receptor optimizes T regulatory cell frequency and facilitates anti-inflammatory responses within the central nervous system." *J Immunol* 188(2): 541-547.
2. Morgan, R. K., B. McAllister, et al. (2007). "Histamine 4 receptor activation induces recruitment of FoxP3+ T cells and inhibits allergic asthma in a murine model." *J Immunol* 178(12): 8081-8089.
3. Tiligada, E., E. Zampeli, et al. (2009). "Histamine H3 and H4 receptors as novel drug targets." *Expert Opin Investig Drugs* 18(10): 1519-1531.
4. Yu, B., Y. Shao, et al. (2010). "Copy number variations of the human histamine H4 receptor gene are associated with systemic lupus erythematosus." *Br J Dermatol* 163(5): 935-940.
5. Zampeli, E. and E. Tiligada (2009). "The role of histamine H4 receptor in immune and inflammatory disorders." *Br J Pharmacol* 157(1): 24-33.

The invention claimed is:

1. A method of treating non-autoimmune uveitis, the method comprising administering an effective amount of a compound which is a histamine 4 receptor antagonist, partial agonist or inverse agonist to a subject having non-autoimmune uveitis.

2. The method according to claim 1 in which the uveitis is subacute, acute or chronic intermediate uveitis, subacute, acute or chronic panuveitis, subacute, acute or chronic posterior uveitis, or subacute, acute or chronic anterior uveitis.

3. The method according to claim 2 in which the uveitis is subacute, acute or chronic anterior uveitis or subacute, acute or chronic posterior uveitis.

4. The method according to claim 1, wherein the compound has a structural core comprising a thienopyrimidine, a furopyrimidine, an aryl or heteroaryl-fused pyrimidine, or a quinazoline group.

5. The method according to claim 1 in which the compound is selected from

A987306 having the structure

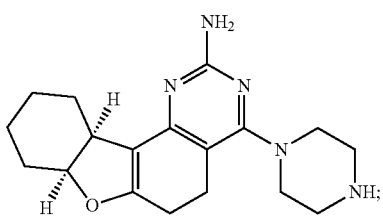 [SMILES: Nc1nc2c(c(N3CCNCC3)n1)CCC1=C2[C@@H]2CCCC[C@@H]2O1]

A943931 having the structure

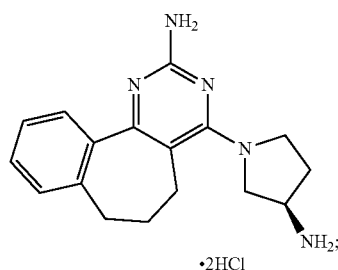 [SMILES: Nc1nc2c(c(N3CC[C@@H](N)C3)n1)CCCc1ccccc1-2]

INCB 38579 (1-(7-(2-amino-6-(4-methylpiperazin-1-yl)pyrimidin-4-yl)-3,4-dihdroisoquinolin-2(1H)-yl)-2-cyclopentylethanone);

994 having the structure

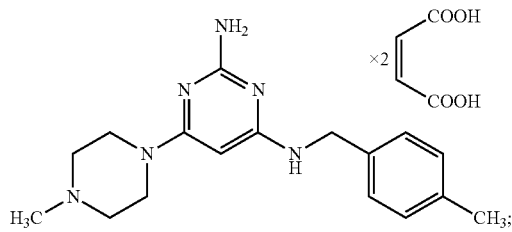

1006 having the structure

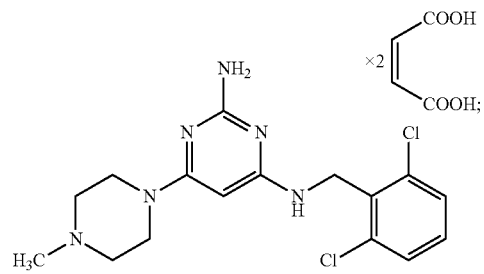

and 1012 having the structure

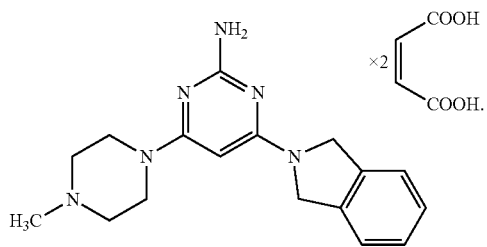 [SMILES: CN1CCN(c2cc(N3Cc4ccccc4C3)nc(N)n2)CC1 ; O=C(O)/C=C\C(=O)O]

6. The method according to any one of claim 1, the method comprising administering the compound to an eye of a subject having non-autoimmune uveitis, in the form of eye drops, by subconjunctival administration, by injection into the eye, or by oral administration.

7. The method according to claim 1 in which wherein the uveitis is non-infectious.

8. The method according to claim 1 in which the uveitis is subacute, acute or chronic intermediate uveitis, panuveitis or posterior uveitis.

9. The method according to claim 1 in which the uveitis is subacute anterior uveitis, or acute anterior uveitis.

10. The method according to claim 1, wherein the compound has a structural core comprising a benzimidazole or a bicyclic heteroaryl-substituted imidazole.

11. The method according to claim 1, wherein the compound has a structural core comprising an indole.

12. The method according to claim 1, wherein the compound is selected from thioperamide; VUF-6002 (1-[(5-chloro-1H-benzimidazol-2-yl)carbonyl]-4-methylpiperazine);

JNJ10191584 having the structure

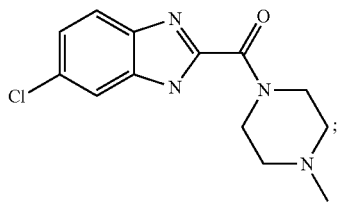 [SMILES: CN1CCN(C(=O)c2nc3ccc(Cl)cc3[nH]2)CC1]

and

JNJ28307474 (5-fluoro-4-methyl-2-{5-methyl-2-[4-(1-methyl-piperidin-4-yl)-butoxy]-pyridin-4yl}-1H-benzoimidazole).

13. The method according to claim 1, wherein the compound is JNJ 7777120(1-[(5-chloro-1H-indol-2-yl)carbonyl]-4-methylpiperazine).

* * * * *